United States Patent [19]

Manabe

[11] Patent Number: 4,950,077
[45] Date of Patent: Aug. 21, 1990

[54] PHOTOELECTRIC MEASURING APPARATUS FOR USE IN AUTOMATIC ANALYZER

[75] Inventor: Sugio Manabe, Kodaira, Japan

[73] Assignee: Olympus Optical Co., Ltd., Japan

[21] Appl. No.: 343,681

[22] Filed: Apr. 27, 1989

[30] Foreign Application Priority Data

Apr. 28, 1988 [JP] Japan .................... 63-56737

[51] Int. Cl.⁵ .......................... G01J 3/42; G01J 3/18
[52] U.S. Cl. .................................................. 356/328
[58] Field of Search ............................... 356/326, 328

[56] References Cited

U.S. PATENT DOCUMENTS

| 3,880,523 | 4/1975 | Thomas . | |
|---|---|---|---|
| 4,571,074 | 2/1986 | Thevenon | 356/328 |
| 4,685,801 | 8/1987 | Minekane | 356/328 |
| 4,781,456 | 11/1988 | Nogami | 356/328 |

FOREIGN PATENT DOCUMENTS

| 2114107 | 11/1971 | Fed. Rep. of Germany . | |
|---|---|---|---|
| 2255300 | 5/1974 | Fed. Rep. of Germany . | |
| 151084 | 11/1979 | Japan | 356/328 |
| 57-52882 | 11/1982 | Japan . | |

OTHER PUBLICATIONS

Lagutin, "A Multichannel Scanning Spectrophotometer", *Bull. Crimean Astrophys. Obs.* (U.S.A.), vol. 60, 1979, pp. 149–153.

*Primary Examiner*—F. L. Evans
*Attorney, Agent, or Firm*—Arnold, White & Durkee

[57] ABSTRACT

A photoelectric measuring apparatus for use in an automatic chemical analyzer in which a plurality of test items are analyzed by using light beams having different wavelengths, including a white light source for emitting a polychromatic light beam, a grating for diffracting the polychromatic light beam into a plurality of light beams having predetermined different wavelengths, a plurality of light guides for guiding the light beams emanating from the grating to a plurality of cuvettes containing test liquids to be analyzed, a plurality of light receiving elements for receiving light beams transmitted through the cuvettes, an additional light guide for guiding a polychromatic light beam emanating from the grating as the zero order light beam to a cuvette via an optical filter having a desired transmission wavelength, and an additional light receiving element for receiving a light beam transmitted through the cuvette.

6 Claims, 4 Drawing Sheets

TPTZ Method

Nitroso·PSAP Method

PHOTOELECTRIC MEASURING APPARATUS FOR USE IN AUTOMATIC ANALYZER

BACKGROUND OF THE INVENTION

1. Field of the Invention and Related Art Statement

The present invention relates to a photoelectric measuring apparatus for use in an automatic chemical analyzer in which a plurality of substances contained in samples, i.e., a plurality of test items, are measured by using a plurality of measuring light beams having different wavelengths.

In Japanese Patent Publication No. 52,982/82, there is disclosed a photoelectric measuring apparatus for use in the chemical analyzer, in which a light beam transmitted through a test liquid is made incident upon a grating and is divided into a plurality of light beams having different wavelengths and these light beams are received by a plurality of photoelectric converting elements, i.e., light receiving elements. In this known photoelectric measuring apparatus, the wavelengths of the light beams emanating from the grating have been previously set and could not be changed simply. Therefore, the photoelectric measuring apparatus could not be easily adopted to the change or increase of the test items to be analyzed as well as to the change or improvement of measuring methods, so that it is necessary to select from the light beams having the previously determined wavelengths a light beam having a wavelength which is closest to a required wavelength. This results in a decrease in the sensitivity and accuracy of measurement. This will be further explained in detail hereinbelow by way of an example.

For instance, it is assumed that the measuring apparatus is designed to produce ten light beams having different wavelengths of 340, 380, 410, 480, 520, 540, 570, 600, 660 and 800 nm. When it is required to change the method of measuring serum iron from the TPTZ method having the maximum absorption at 600 nm as illustrated in FIG. 1 to the nitroso PSAP method having the maximum absorption at 750 nm shown in FIG. 2. In this case, since the photoelectric measuring apparatus does not generate the light beam having the wavelength of 750 nm, the PSAP method has to be carried out by using the light beam having the wavelength of 800 nm. Then, it is apparent that the measuring sensitivity is decreased by about 25% upon being compared with the case in which the standard wavelength of 750 nm is used. Therefore, the accuracy of the measurement is also decreased to a great extent.

In order to avoid the above mentioned drawback it may be considered that a larger number of light beams than those which are initially required are generated by the grating. However, this solution has another drawback that the number of light receiving elements becomes large and the photoelectric measuring apparatus is liable to be complicated in construction, large in size and expensive in cost.

SUMMARY OF THE INVENTION

The present invention has for its object to provide a novel and useful photoelectric measuring apparatus for use in the automatic analyzer, in which one or more light beams having desired wavelengths can be easily obtained by means of the simple construction, and thus the photoelectric measuring apparatus can be easily adopted to the change and increase of the test items and the change of the measuring method, while high sensitivity and accuracy of the measurement can be maintained.

According to the invention, a photoelectric measuring apparatus for use in an automatic analyzer utilizing a plurality of light beams having different wavelengths, comprises a light source for emitting a polychromatic light beam;

a grating for receiving the polychromatic light beam and generating a plurality of light beams having predetermined different wavelengths as higher order light beam as well as a polychromatic light beams as a zero order light beam; and optical filter means for deriving a light beam having a desired wavelength from the polychromatic light beam of the zero order light beam emanating from the grating.

According to the invention, when the polychromatic light beam is made incident upon the grating, a spectrum emanating from the grating contains a plurality of light beams having different wavelengths as higher order beams and at the same time the polychromatic light beam is derived from the grating as the zero order light beam. That is to say, the zero order light beam has the same spectrum range as the incident polychromatic light beam. According to the invention, this zero order light beam is transmitted through the optical filter means, such as a color filter and an interference filter, to derive a monochromatic light beam having a desired wavelength which could not be obtained directly from the grating.

DESCRIPTION OF THE PREFERRED EMBODIMENTS

Figure 1:
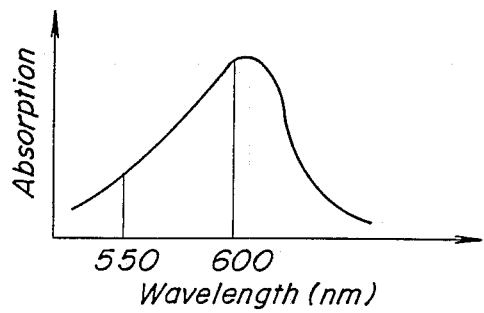
FIG. 1 is a graph showing the light absorption property of the TPTZ method.
Figure 2:
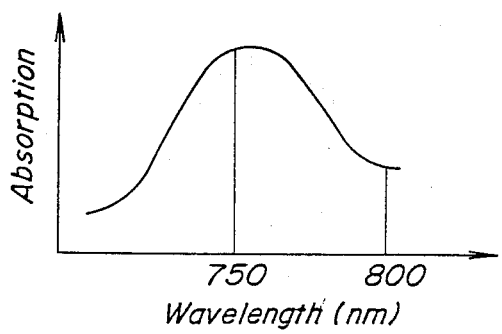
FIG. 2 is a graph illustrating the light absorption property of the nitroso-PSAP method.
Figure 3:
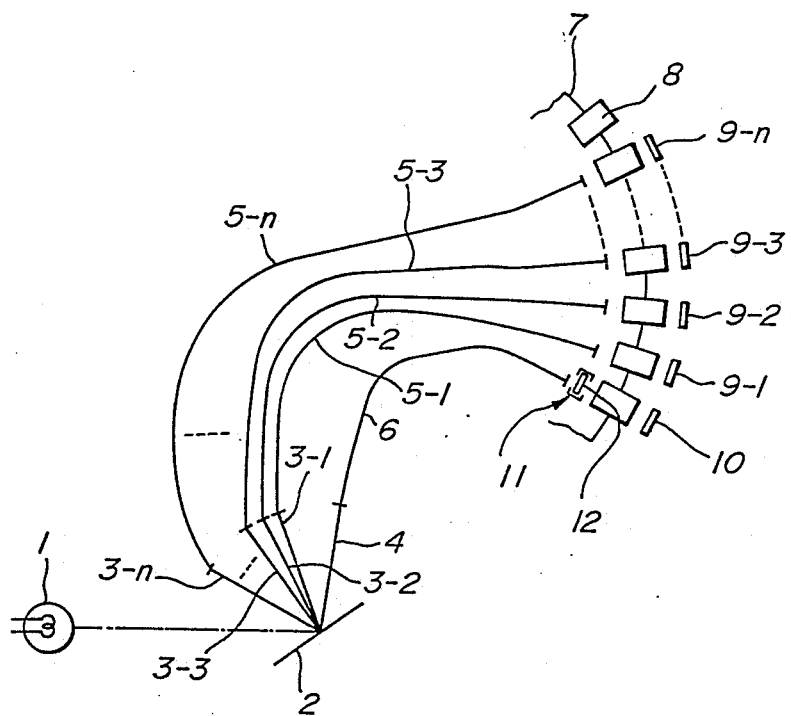
FIG. 3 is a schematic view depicting an embodiment of the photoelectric measuring apparatus according to the invention.

FIG. 3 is a schematic view showing an embodiment of the photoelectric measuring apparatus according to the invention. In this embodiment, a polychromatic light beam, e.g. a white light beam emitted from a white light source 1 is made incident upon a grating 2. Then, a plurality of measuring light beams 3-1, 3-2, ... 3-n having different wavelengths $\lambda_1, \lambda_2 ... \lambda_n$ are reflected from the grating 2 in different directions. At the same time, a zero order light beam 4 emanates from the grating 2. It should be noted that the zero order light beam 4 contains all the wavelengths in the incident white light beam. The measuring light beams 3-1, 3-2 ... 3-n are made incident upon inlet end faces of light guides 5-1, 5-2 ... 5-n, respectively, and the zero order light beam 4 is made incident upon an inlet end face of a light guide 6. Exit end faces of these light guides 3-1, 3-2 ... 3-n and 6 are arranged along a reaction line defined by a rotatable cuvette wheel on which a number of cuvettes 8 containing test liquids are arranged. The measuring light beams 3-1, 3-2 ... 3-n emitted from the exit end faces of the light guides 5-1, 5-2 ... 5-n are transmitted through the cuvettes 9-1, 9-2 ... 9-n, respectively and are then made incident upon light receiving elements 9-1, 9-2 ... 9-n. In the present embodiment, there is arranged an optical filter holding member 11 between the exit end face of the light guide 6 transmitting the zero order light beam 4, and an optical filter 12 is detachably inserted into the optical filter holding member 11. Then, a monochromatic measuring light beam having a desired wavelength determined by the optical filter emanates from the optical filter 12 and is made incident upon a cuvette 8 on the cuvette wheel 7. The light beam transmitted through the cuvette 8 is made incident upon a light receiving element 10. By rotating the cuvette wheel 7, the cuvettes 8 are successively passed through the measuring positions situating between the exit end faces of the light guides 5-1, 5-2 ... 5-n and 6 and the light receiving elements 9 1, 9-2, ... 9-n and 10, respectively. Output signals from the light receiving elements 9-1, 9-2 ... 9-n and 10 are supplied to a signal processing circuit not shown and an output signal corresponding to a given test item is selected.

In the embodiment so far explained, by inserting an optical filter 12 into the filter holding member 11, it is possible to obtain a measuring light beam having a wavelength other than the previously set wavelengths $\lambda hd\ 1, \lambda_2 ... \lambda_n$, so that the increase in the test items and the alternation or improvement of the measuring method can be easily taken over, and the measurement can be carried out at the high sensitivity and accuracy.

Figure 4:
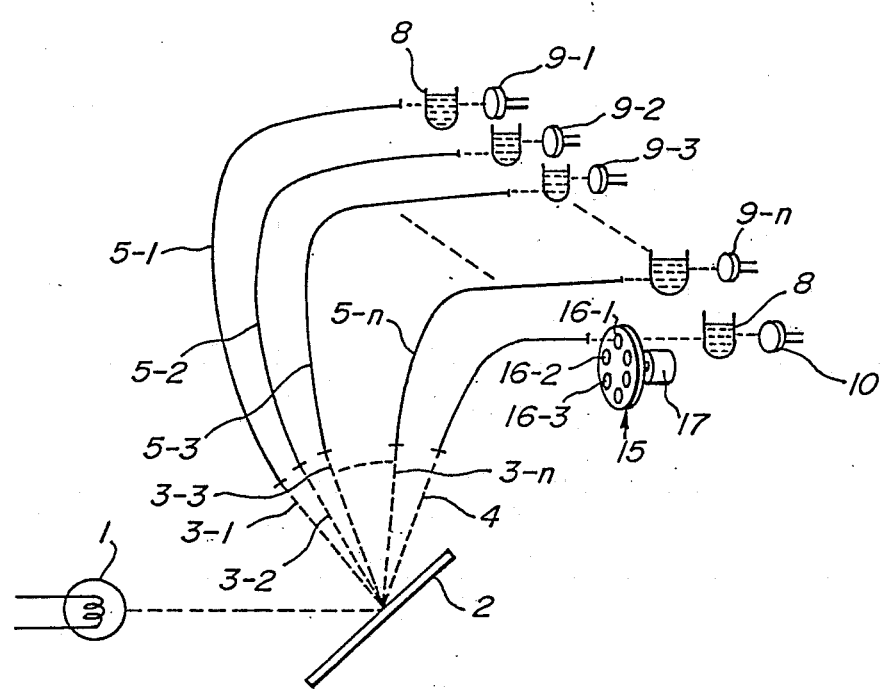
FIG. 4 is a schematic view showing another embodiment of the apparatus according to the invention.
Figure 5:
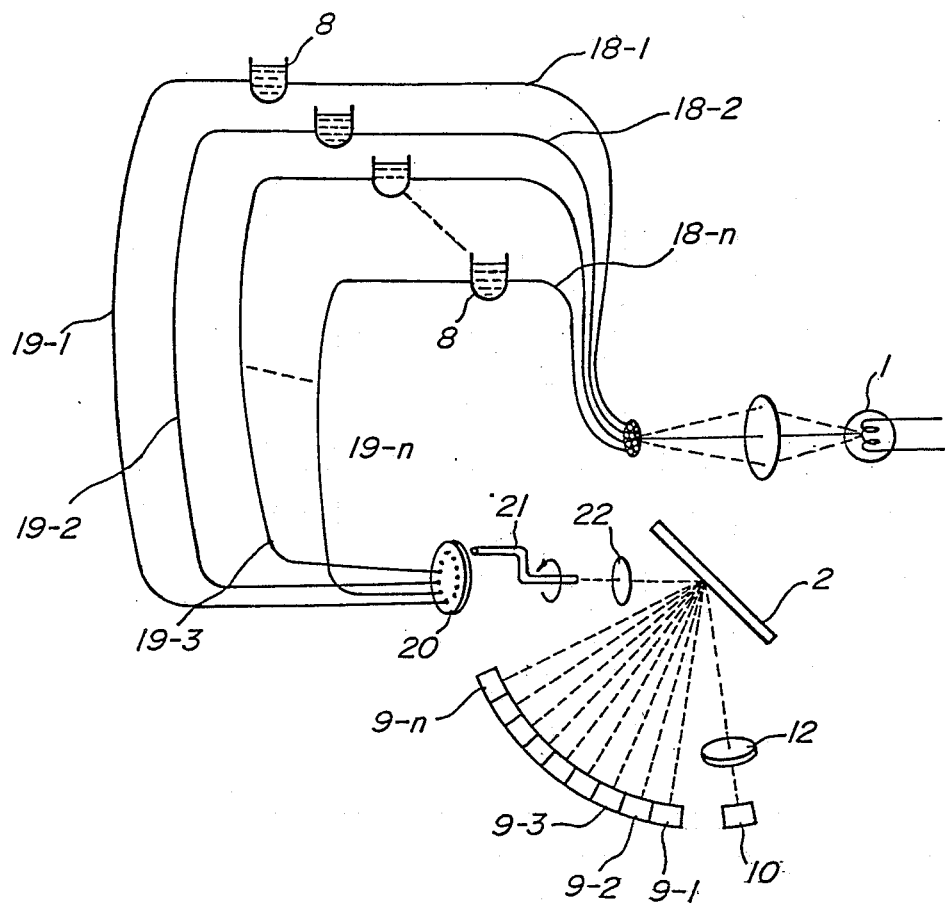
FIG. 5 is a schematic view illustrating still another embodiment of the apparatus according to the invention.

In the above explained embodiment, the optical filter 12 is detachably inserted into the optical filter supporting member 11, but a rotary filter 15 having a plurality of optical filter elements 16-1, 16-2 ... installed therein and being driven by a motor 17 may be arranged instead of the filter supporting member 11 as illustrated in FIG. 4. Further, in the above embodiment, the polychromatic light beam is diffracted into a plurality of measuring light beams by means of the grating 2 and then the measuring light beams are made incident upon the test liquids. However, the polychromatic light beam emitted from the white light source 1 may be first made incident upon the test liquids contained in the cuvettes 8 as shown in FIG. 5 via optical fibers 18-1, 18-2 ... 18-n. The measuring light beams transmitted through the cuvettes 8 are then made incident upon optical fibers 19-1, 19-2 ... 19-n, respectively. The outlet end faces of the these optical fibers 19-1, 192 ... 19-n are arranged along a circle in a disc 20, and a crank shaped optical fiber 21 is arranged rotatably about a center axis of the disc 20 so that the measuring light beams are successively selected by the crank-shaped optical fiber 21. The light beams thus selected by the crank-shaped optical fiber 21 are successively made incident upon the grating 2 via a lens 22. Then, each of the measuring beams is diffracted into a plurality of light beams having different wavelengths and these light beams are made incident upon the light receiving elements 9-1, 9-2 ... 9-n. At the same time, the zero order light beam emanates from the grating 2 and is made incident upon the light receiving element 10 via the optical filter 12.

As explained above, according to the invention in addition to a plurality of measuring beams having predetermined different wavelengths, a measuring light beam having a desired wavelength other than said wavelengths can be obtained by passing the zero order light beam emanating the grating through an optical filter. Therefore, the measuring apparatus can be easily adopted to an increase in the test items and a change in the measuring method, and the measuring can be performed in an accurate and precise manner.

What is claimed is:

1. A photoelectric measuring apparatus for use in an automatic analyzer utilizing a plurality of light beams having different wavelengths, comprising:
    a light source for emitting a polychromatic light beam;
    a grating for receiving said polychromatic light beam and generating a plurality of light beams having predetermined different wavelengths as higher order light beams, and a polychromatic light beam as a zero order light beam;
    a plurality of light guides for guiding said plurality of light beams having predetermined different wavelengths to a plurality of cuvettes which contain test liquids to be analyzed and which are arranged along a reaction line;
    a plurality of light receiving elements for receiving light beams transmitted through said plurality of cuvettes;
    optical filter means for deriving a light beam having a desired wavelength from said polychromatic light beam of the zero order light beam emanating from the grating;
    a light guide for guiding the polychromatic light beam of the zero order light beam via the optical filter means to a cuvette; and
    a light receiving element for receiving a light beam transmitted through said cuvette.

2. The apparatus of claim 1, wherein said optical filter means comprises an optical filter holding member and an optical filter detachably inserted into said optical filter holding member.

3. The apparatus of claim 1, wherein said optical filter means comprises a rotary filter having a plurality of optical filter elements installed therein and a motor for rotating the rotary filter.

4. A photoelectric measuring apparatus for use in an automatic analyzer utilizing a plurality of light beams having different wavelengths, comprising:
    a light source for emitting a polychromatic light beam;
    a first set of light guides for guiding the polychromatic light beam from the light source to a plurality of cuvettes which contain test liquids to be analyzed and are fed along a reaction line;
    a second set of light guides for guiding light beams transmitted through the cuvettes to outlet end faces which are arranged along a circle having a center axis;
    a crank-shaped optical fiber arranged rotatably about the center axis of the circle and selecting successively the light beams transmitted through the second set of light guides;
    a grating for receiving the light beams transmitted through the second set of light guides and generating a plurality of light beams having predetermined different wavelengths as higher order light beams and a polychromatic light beam as a zero order light beam;
    optical filter means for deriving a light beam having a desired wavelength from said polychromatic light beam of the zero order light beam emanating from the grating;

a plurality of light receiving elements for receiving the higher order light beams; and a single light receiving element for receiving the zero order light beam via said optical filter means.

5. The apparatus of claim 4, wherein said optical filter means comprises an optical filter holding member and an optical filter detachably inserted into said optical filter holding member.

6. The apparatus of claim 4, wherein said optical filter means comprises a rotary filter having a plurality of optical filter elements installed therein and a motor for rotating the rotary filter.

* * * * *